(12) United States Patent
Giroux et al.

(10) Patent No.: US 8,555,423 B2
(45) Date of Patent: Oct. 15, 2013

(54) GOGGLE ATTACHMENT SYSTEM FOR A PROTECTIVE HELMET

(75) Inventors: George T. Giroux, Hailey, ID (US); Hans Lindauer, Portland, OR (US); James A. Chilson, Hailey, ID (US)

(73) Assignee: Smith Optics, Inc., Ketchum, ID (US)

( * ) Notice: Subject to any disclaimer, the term of this patent is extended or adjusted under 35 U.S.C. 154(b) by 189 days.

(21) Appl. No.: 13/009,804

(22) Filed: Jan. 19, 2011

(65) Prior Publication Data

US 2012/0180203 A1 Jul. 19, 2012

(51) Int. Cl.
*A42B 1/24* (2006.01)

(52) U.S. Cl.
USPC .............................................. 2/422

(58) Field of Classification Search
USPC ............... 2/422, 431, 10, 424, 426, 438, 452, 2/909; 29/428
See application file for complete search history.

(56) References Cited

U.S. PATENT DOCUMENTS

| 860,322 | A | | 7/1907 | Paroubek | |
|---|---|---|---|---|---|
| 2,903,700 | A | * | 9/1959 | Finken et al. | ........................ 2/10 |
| 3,237,203 | A | * | 3/1966 | Nielsen | ............................... 2/10 |
| D213,085 | S | | 1/1969 | Wyckoff | |
| 3,783,452 | A | * | 1/1974 | Benson et al. | ..................... 2/6.4 |
| 4,042,974 | A | | 8/1977 | Morgan et al. | |
| 4,136,403 | A | | 1/1979 | Walther et al. | |
| D266,626 | S | | 10/1982 | Gooding | |
| 4,686,712 | A | * | 8/1987 | Spiva | ................................. 2/10 |
| 4,713,844 | A | * | 12/1987 | Westgate | ........................ 2/411 |
| 4,764,989 | A | * | 8/1988 | Bourgeois | ........................ 2/422 |
| 4,918,753 | A | * | 4/1990 | Mermillod | ......................... 2/10 |
| D400,555 | S | | 11/1998 | Wang | |
| 5,987,652 | A | * | 11/1999 | Fowler | .............................. 2/424 |
| D428,906 | S | | 8/2000 | Bolle | |
| D455,522 | S | | 4/2002 | Royes et al. | |
| D464,174 | S | | 10/2002 | Lu | |
| 6,490,729 | B1 | | 12/2002 | Dondero | |
| D482,500 | S | | 11/2003 | Ho | |
| 6,708,340 | B1 | | 3/2004 | Dondero | |

(Continued)

FOREIGN PATENT DOCUMENTS

FR 2838307 A1 10/2003
JP 2000239916 9/2000

(Continued)

OTHER PUBLICATIONS

International Search Report and Written Opinion dated May 23, 2012 for Application No. PCT/US2011/055726.

*Primary Examiner* — Khoa Huynh
*Assistant Examiner* — Anna Kinsaul
(74) *Attorney, Agent, or Firm* — Dorsey & Whitney LLP

(57) ABSTRACT

Goggles, protective wear, and methods attaching and detaching a goggle are disclosed. In a described example, protective wear includes a goggle and a helmet. The goggle include first and second strap attachments coupled to a strap. The first strap attachment is pivotally connected to a goggle assembly and the second strap attachment has a post. The helmet includes an anchor positioned in an opening in the helmet and is oriented to position an anchor channel to be in line with a recess formed on an exterior of the helmet. The anchor is configured to receive the post and pivotally secure the post therein to attach the goggle to the helmet. The anchor is further configured to release the post responsive to the second strap attachment pulled in a direction substantially parallel with the anchor channel of the anchor.

23 Claims, 10 Drawing Sheets

(56) References Cited

U.S. PATENT DOCUMENTS

| | | | |
|---|---|---|---|
| 6,845,548 B1 * | 1/2005 | Lin | 24/265 BC |
| 6,970,691 B2 | 11/2005 | Thompson | |
| D515,615 S | 2/2006 | Fecteau et al. | |
| D535,059 S | 1/2007 | Lam | |
| 7,260,850 B2 | 8/2007 | Ambuske et al. | |
| D556,951 S | 12/2007 | Gath | |
| D610,602 S | 2/2010 | Yun | |
| D616,915 S | 6/2010 | Silveria et al. | |
| D628,346 S | 11/2010 | Petzl | |
| D645,210 S | 9/2011 | Chilson et al. | |
| D655,048 S | 2/2012 | Moeller et al. | |
| D675,249 S | 1/2013 | Giroux | |
| 2005/0183190 A1 | 8/2005 | Hussey | |
| 2006/0059606 A1 | 3/2006 | Ferrara | |
| 2007/0083967 A1 | 4/2007 | Crossman et al. | |
| 2007/0130672 A1 | 6/2007 | Beddoe et al. | |
| 2008/0052808 A1 | 3/2008 | Leick et al. | |
| 2008/0172778 A1 * | 7/2008 | Lysogorski | 2/436 |
| 2009/0300830 A1 * | 12/2009 | Mage | 2/441 |
| 2010/0325784 A1 * | 12/2010 | Abbott et al. | 2/422 |
| 2011/0072564 A1 * | 3/2011 | Krauter | 2/422 |
| 2011/0113535 A1 | 5/2011 | Lebel et al. | |
| 2011/0265237 A1 * | 11/2011 | Lazar et al. | 2/10 |
| 2012/0180202 A1 * | 7/2012 | McNeal | 2/422 |
| 2012/0185989 A1 | 7/2012 | Higgins | |

FOREIGN PATENT DOCUMENTS

| | | |
|---|---|---|
| KR | 100918879 | 9/2009 |
| WO | 2008/006357 A2 | 1/2008 |
| WO | 2009/092368 A2 | 7/2009 |
| WO | 2010/076817 A1 | 7/2010 |
| WO | WO 2010076817 A1 * | 7/2010 |
| WO | 2012/099631 A1 | 7/2012 |

* cited by examiner

# GOGGLE ATTACHMENT SYSTEM FOR A PROTECTIVE HELMET

TECHNICAL FIELD

Embodiments of the invention relate generally to goggles and helmets, and more specifically, in one or more of the illustrated embodiments, to goggle attachment systems for attaching a goggle to a helmet.

BACKGROUND OF THE INVENTION

Protective gear may be worn to protect the person from injury during participation in an activity. Common examples of protective gear include helmets and goggles, which are often worn together to protect the wearer's head and eyes from injury. For example, helmets and goggles worn during snow sports are now considered standard protective wear and provide head and eye protection in the event of a fall or crash. The helmet and goggle may also protect the wearer from equipment (e.g., skis, poles, snowboards, boots) that may come loose and strike the wearer in the head or face. Significant injury can result if the head and eyes are not protected.

Due to the frequency of helmets and goggles being worn together, they are often designed with each other in mind. For example, goggles may be designed so that the goggle may fit comfortably on the face although a helmet may otherwise interfere with the positioning of the goggle on the wearer's face and the positioning of the goggle strap to hold the goggle in place.

In another example, helmets may include a mechanism for clipping the goggle strap to the rear portion of a helmet so that in the event the goggle is displaced, the goggle strap (and thereby the goggle) remains clipped to the helmet. Although the mechanism can prevent the goggle from being lost, it does require the wearer to clip the goggle strap to the mechanism in the first place. Additionally, attaching and detaching the goggle from the helmet when the strap is clipped-in may also take more effort than desirable because the clips are designed to prevent the goggle from accidentally detaching from the helmet. For example, detaching the goggle requires the strap to be unclipped, which may involve the wearer removing the helmet in order to view the rear portion of the helmet to unclip the strap.

Therefore, it may be desirable to have a goggle attachment system for goggles that are worn with helmets that provides easy attachment and detachment of the goggles.

DETAILED DESCRIPTION OF PREFERRED EMBODIMENTS

The present application describes a goggle attachment system and a method of attaching goggles to helmets. Many specific details of certain embodiments of the invention are set forth in the following description and the Figures provide a thorough understanding of such embodiments. One skilled in the art, however, will understand that the present invention may have additional embodiments and that other embodiments of the invention may be practiced without several of the details and components described in the following description.

Figure 1A:
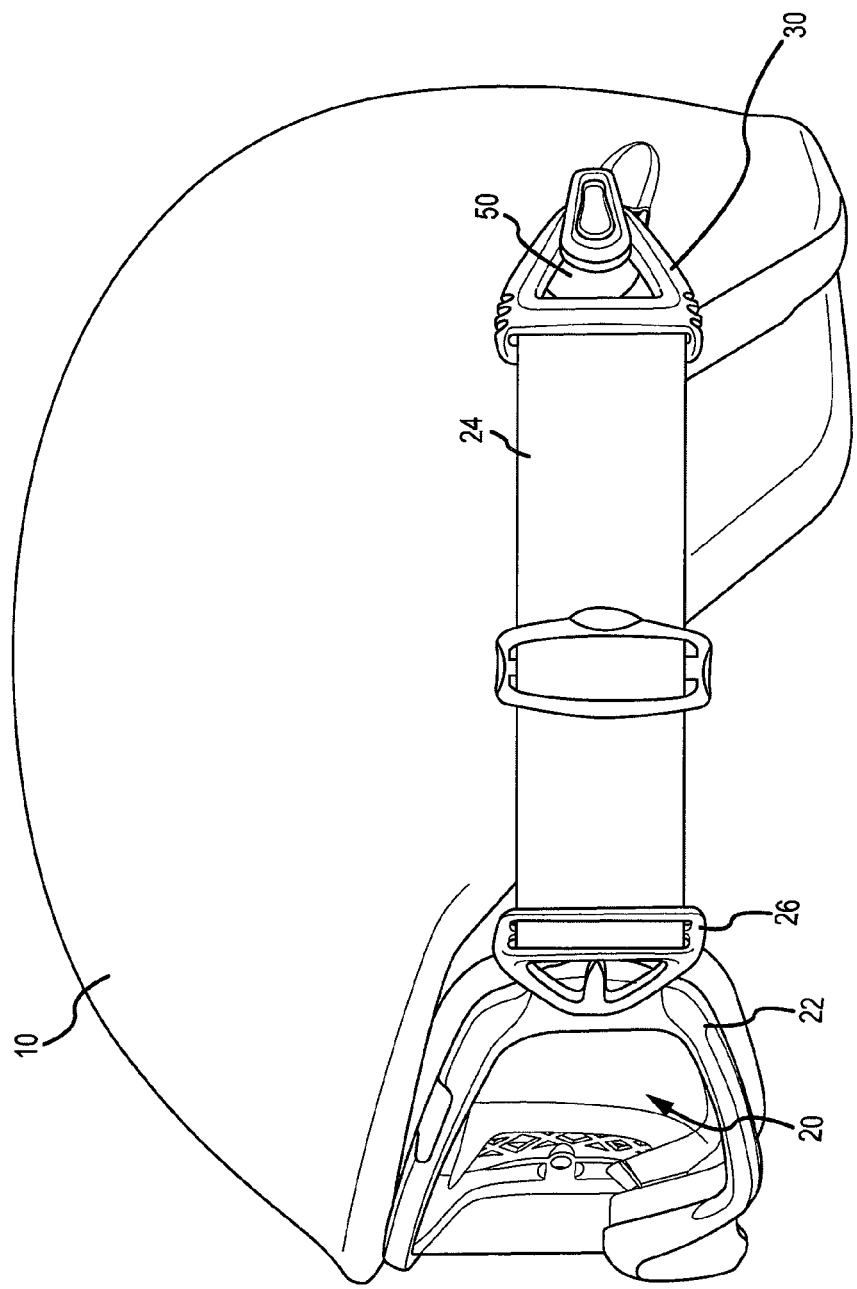
FIGS. 1A and 1B are perspective drawings of a helmet and goggle having a goggle attachment system according to an embodiment of the invention.
Figure 1B:
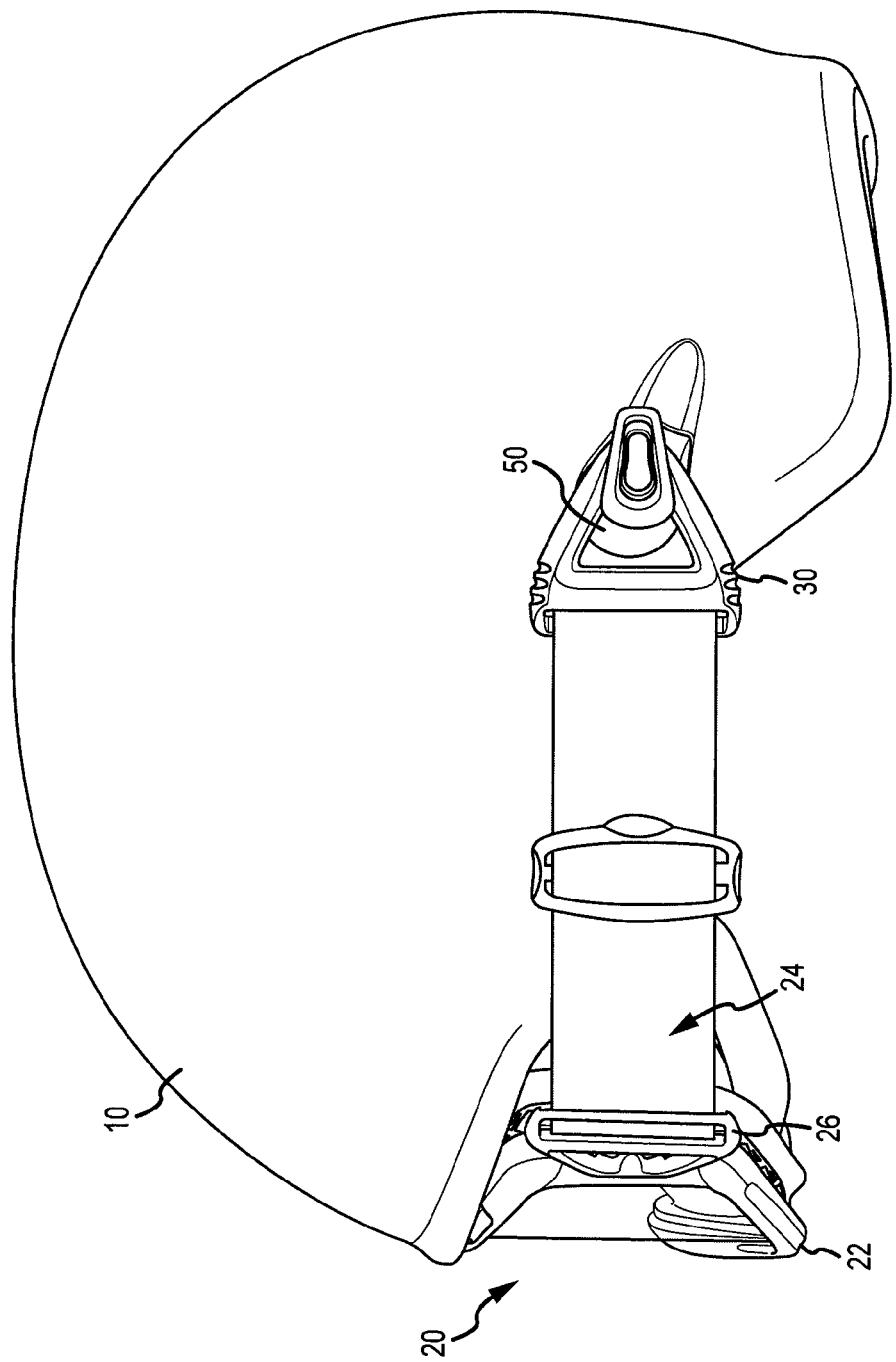

FIGS. 1A and 1B illustrate a goggle attachment system according to an embodiment of the invention for a helmet 10 and goggle 20. The helmet 10 and goggle 20 may be worn during activities, for example, skiing or snowboarding. Goggle 20 has a lens assembly 22 to which resilient strap 24 is attached by strap connector 26. The resilient strap 24 may be connected to the strap connector 26 by securing the strap 24 through a loop of the strap connector 26. In other embodiments, the strap 24 may be attached to the strap connector 26 by other techniques, for example, molded into the strap connector 26. The strap 24 may be adjustable, for example, using adjustment mechanisms commonly known. The strap connector 26 may be pivotally attached to the lens assembly 22 of the goggle 20, as shown in the embodiment of FIGS. 1A and 1B. A pivotal attachment of the strap connectors 26 to the goggle 20 has a benefit of allowing for the straps 24 to pivot and achieve an angle relative to the lens assembly 22 to comfortably position the goggle 20 on a variety of face shapes and avoid strap binding. Other strap attachment techniques to the lens assembly 22 may be used as well without departing from the scope of the present invention. The lens assembly 22 may be a framed, frameless, or other goggle design. The lens assembly may include a goggle lens and a lens structure attached to the goggle lens which provides attachment to the strap connector 26.

A strap connector 30 attached to the strap 24 may be, as will be explained in more detail below, removably and pivotally attached to an anchor 50 of the helmet 10. The strap 24 may be connected to the strap connector 30 through a loop of the strap connector 30, molded into the strap connector 26, or other design. In the embodiment illustrated in FIGS. 1A and 1B, the strap 24 is attached to the strap connector 30 through a loop. The opposed dual-pivoting attachment to the lens assembly 22 and of the strap connector 30 to the helmet 10 may allow the goggle to independently adjust to the particularities of a wearers facial features and provide a comfortable fit. Although not illustrated in FIGS. 1A and 1B, a second resilient strap 24 and strap connector 26 are attached to the opposite side of the lens assembly 22 of the goggle 20. In some embodiments, a second anchor 50 is located on the opposite side of the helmet 10 to which a second strap connector 30 is removably and pivotally attached.

Figure 2A:
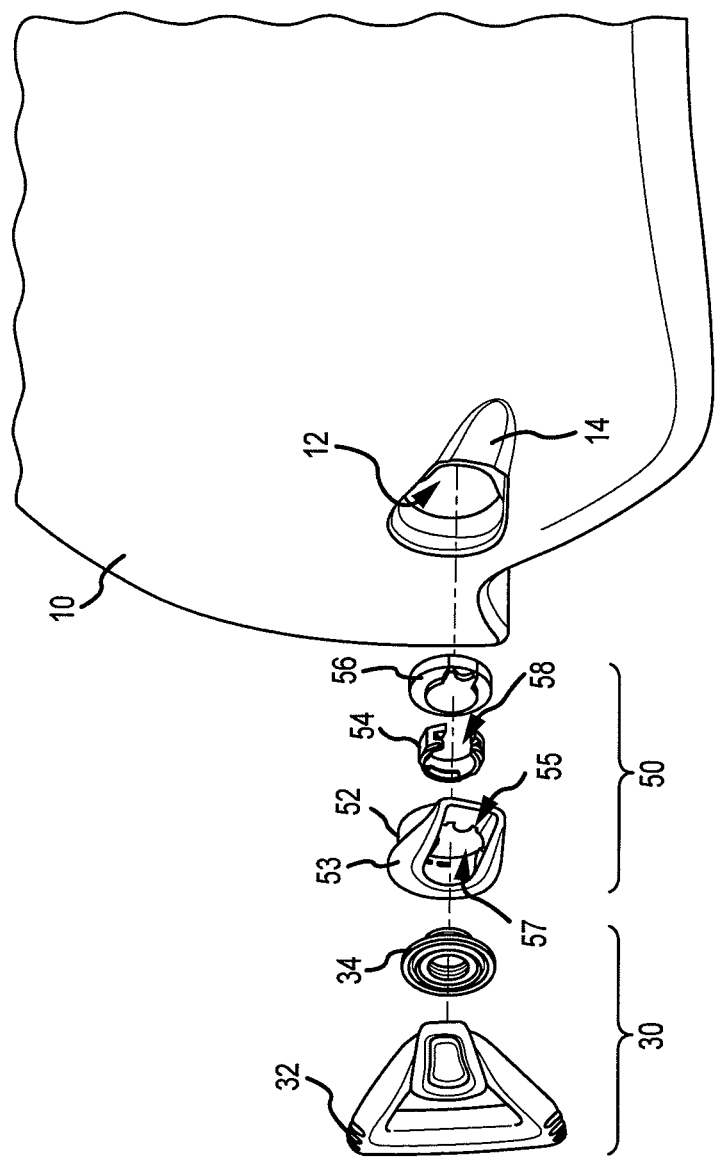
FIGS. 2A-2C are perspective drawings of a goggle attachment system according to an embodiment of the invention.

FIG. 2A illustrates a strap connector 30 and anchor 50 according to an embodiment of the invention. The strap connector 30 includes a strap pull 32 and a post 34 that is attached to the strap pull 32. The post 34, as shown in the embodiment of FIG. 2A may be attached to the strap pull 32. In some embodiments, the post 34 is integrally formed with the strap pull 32. The anchor 50 is configured to receive and pivotally secure the post 34. The anchor 50 of the embodiment illustrated in FIG. 2A includes an anchor fitting 52, and an anchor clip 54 and anchor cover 56. The anchor cover 56 engages the anchor fitting 52 to retain the anchor clip 54 in the anchor fitting 52. In some embodiments, magnets are included in post 34 and the anchor cover 56 to facilitate positioning of the post 34 proximate the anchor 50 and guide the post 54 into the anchor opening 55 to be clipped in the anchor 50. Examples of mechanisms utilizing a clip and cover, for example, anchor clip 54 and anchor cover 56, and magnetic attraction to help guide a post into a latch are designed and manufactured by Fidlock GmbH, for example, as described in International Patent Publication WO2008/006357 and WO2009/092368.

The anchor fitting 52 may include a beveled surface 53, as illustrated in FIG. 2A. The anchor 50 is positioned in an opening 12 formed in the helmet 10. A recess 14 is formed adjacent the opening 12, and as will be explained in more detail below, may facilitate pulling the strap pull 32 and post 34 free from the anchor 50, thereby detaching the strap connector 30 from the helmet 10.

The anchor fitting 52 may be configured to have an anchor opening 57 that receives the post 34 so that it may be clipped by anchor clip 54. The anchor clip 54 includes a split 58 and is configured to hold the post 34 within the anchor 50 but release the post 34 when it is pulled in a direction through the split 58. When clipped in the anchor 50, the post 34 is secured but is still allowed to rotate within the anchor opening 57 thereby allowing the strap connector 30 to rotate while engaged in the anchor 50. The anchor fitting 52 is further configured to have a detachment channel 55 that allows the post 34 to be pulled free of the anchor 50 so that the strap connector 30 may be detached.

Figure 2B:
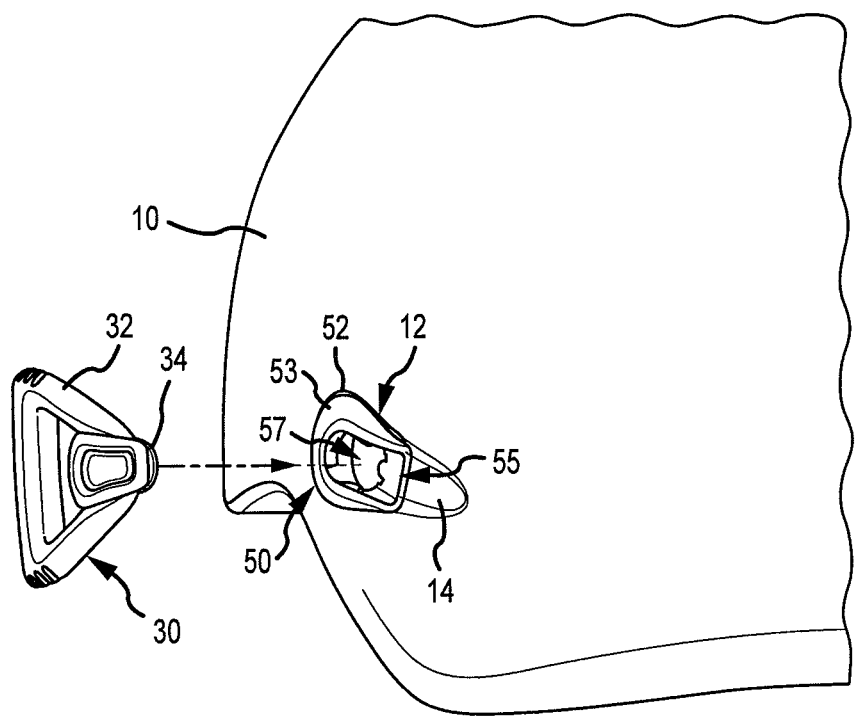
Figure 2C:
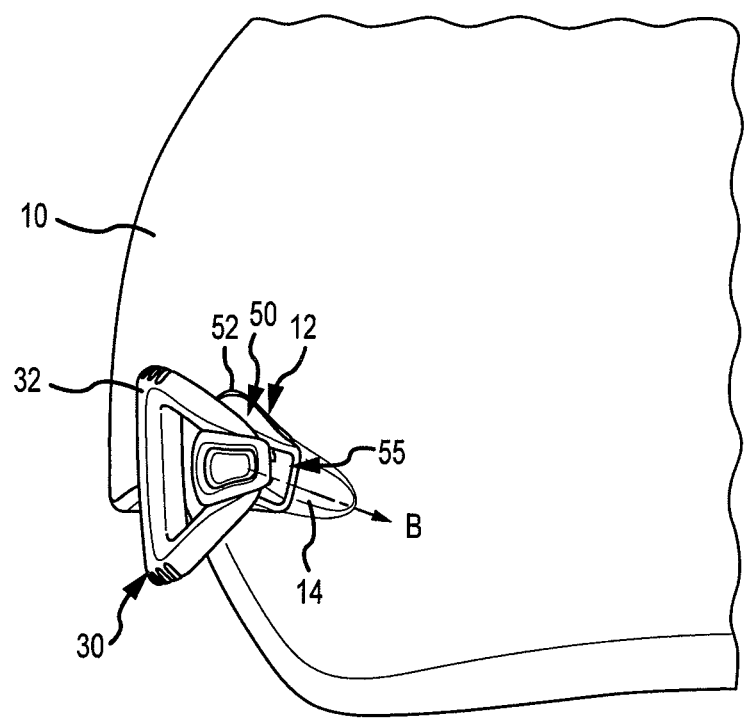

In operation, to attach the strap connector 30 to the anchor 50, the strap connector 30 is moved in a generally perpendicular direction toward the anchor opening 57, for example, direction A shown in FIG. 2B, until the post 34 is inserted into the anchor opening 57 until the post is engaged and pivotally secured in the anchor 50 (e.g., by anchor clip 54). To detach the strap connector 30, the post is pulled free from the anchor 50 by pulling the strap pull 32 (and thereby the post 34) in a direction generally parallel to the length of the detachment channel 55, for example, direction B shown in FIG. 2C. The post 34 is pulled through the split 58 and released from the anchor clip 54 so that the strap connector 30 can be detached from the helmet 10. In some embodiments, the post 34 may be attached to the anchor 50 in addition or in the alternative to perpendicular insertion into the anchor 50 by sliding the post 34 along the detachment channel 55 into the anchor opening 57 where the post is engaged.

The previously described embodiment provides an example of an anchor 50 having a specific clip and cover configuration. However, other embodiments may utilize anchors of other designs, for example, rather than the specific configuration of the anchor clip 54 and anchor cover 56 illustrated in FIG. 2A, an anchor can utilize alternatively configured clips and covers. Moreover, the anchor 50 may utilize other mechanisms for receiving, engaging, and pivotally securing the post 34, for example, spring engaged latches, catches, slots, and other mechanisms now known or later developed. Therefore, the invention is not limited to the specific embodiment illustrated and described with reference to FIG. 2A.

Figure 3A:
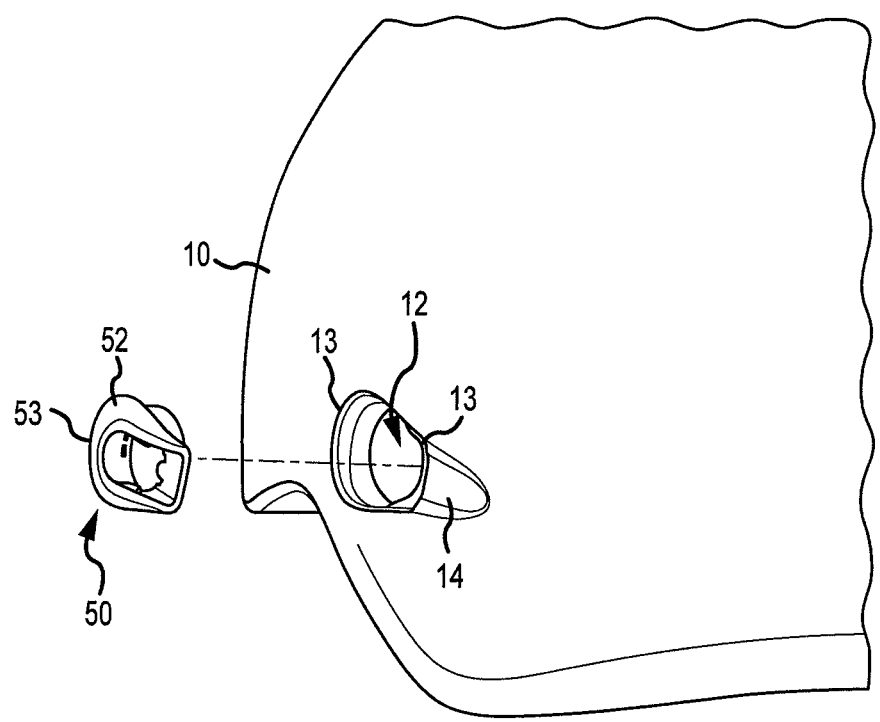
FIGS. 3A and 3B are perspective drawings of an anchor fitting of the goggle attachment system according to an embodiment of the invention.
Figure 3B:
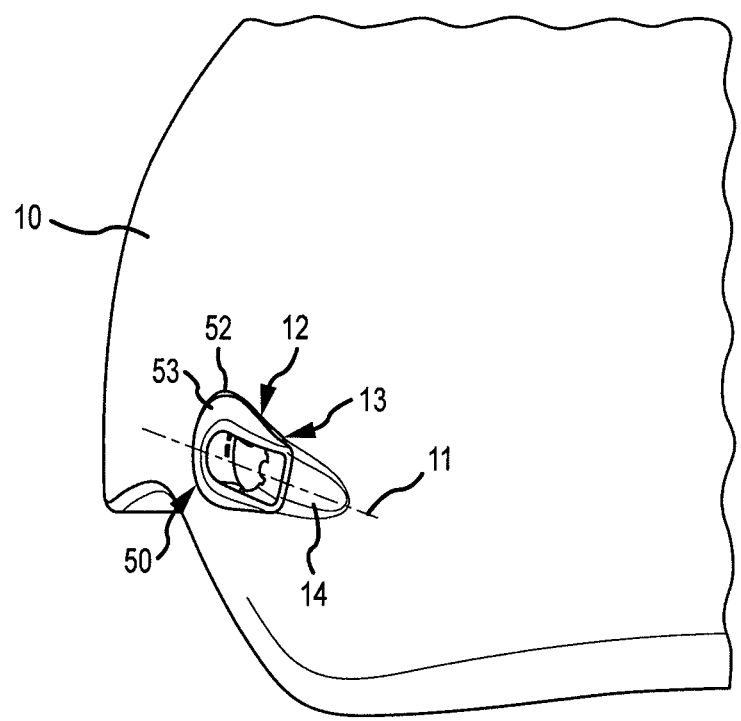

FIG. 3A illustrates the opening 12 of the helmet 10 in which the anchor 50 is positioned. The anchor 50 is shown with anchor fitting 52, anchor clip 54, and anchor cover 56 of FIG. 2A assembled. The anchor 50 fits into the opening 12 with the anchor fitting 52 engaging an anchor fitting recess 13, as shown in FIG. 3B. The opening 12 in which the anchor 50 is positioned may be formed through a shell of the helmet 10 and a cavity formed in a helmet liner. The cavity may partially extend or extend all the way through the helmet liner to house at least a portion of the anchor.

When positioned in the opening 12, as shown in FIG. 3B, the detachment channel 55 is oriented to line up with the recess 14, for example, in-line with a longitudinal axis 11 of the recess 14. This may facilitate detaching the strap connector 30 from the anchor 50 when it is pulled in a direction along the detachment channel 55, for example, direction B shown in FIG. 3B. In some embodiments, the recess 14 may be angled downward, for example, relative to a horizontal plane of the helmet when the helmet is worn, to further facilitate detachment of the post (and the strap connector 30) from the anchor 50.

The anchor 50 may fit in the opening 12 and the recess 13 so that the anchor fitting 52 is recessed relative to an outer surface of the helmet 10 and the beveled surface 53 provides a relatively smooth transition from the helmet surface to the anchor 50. In addition to being esthetically pleasing, such a configuration of the anchor fitting 52, and opening 12 and recess 13, results in a profile for the anchor 50 that may reduce surface abruptness between the anchor 50 and the helmet surface. Additionally, in embodiments having the anchor 50 located on the helmet to receive a post located on the strap connector (i.e., part of the goggle) may help eliminate protruding features on the helmet 10.

Figure 4A:
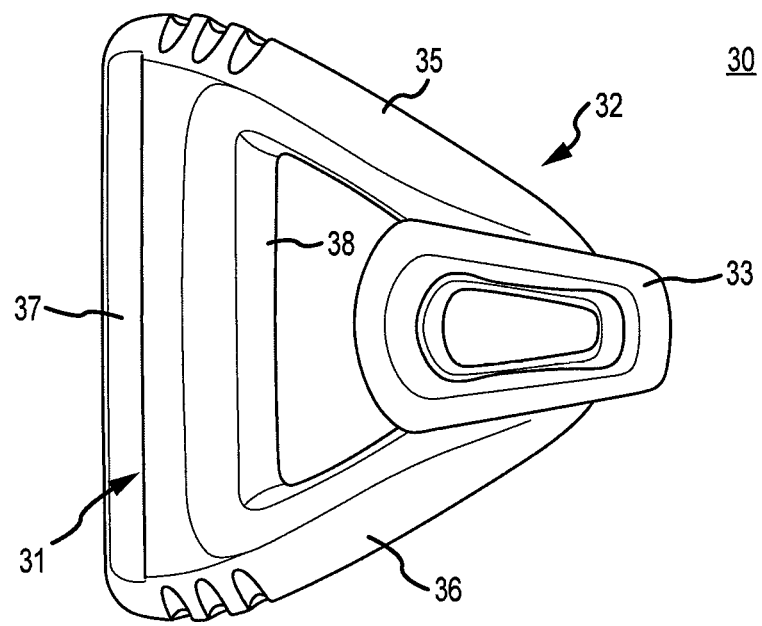
FIGS. 4A and 4B are perspective drawings of a goggle strap attachment post of a goggle attachment system according to an embodiment of the invention.
Figure 4B:
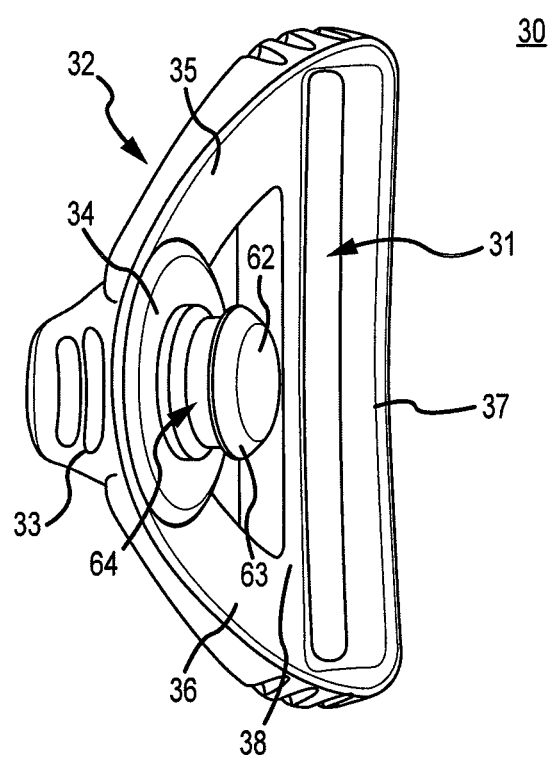

FIGS. 4A and 4B illustrate the strap connector 30 according to an embodiment of the invention. A strap pull 32 is configured to have a generally triangularly shape formed from members 35, 36, and 38. The member 38 forms a loop 31 with cross member 37 through which the resilient strap 24 is attached to the strap connector 30. A pull portion 33 of the strap pull 32 may facilitate grabbing of the strap connector 30, for example, to pull the strap connector free of the anchor 50. The pull portion 33 may be formed with ridges on the surface to assist with gripping the strap connector. The post 34 is configured to have a button portion 62 and a groove 64. The button portion 62 may have a beveled surface 63 to facilitate insertion into the anchor 50 and the groove 64 is engaged, for example, anchor clip 54, to clip the post 34 and thereby the strap connector 30 in the anchor 50. As previously described, the post 34 may be attached to the strap pull 32. For example, the post 34 and strap pull 32 may be formed with matching threaded portions (not shown) so that the two are screwed together. In some embodiments, the post 34 may be integrally formed with the strap pull 32.

Figure 5:
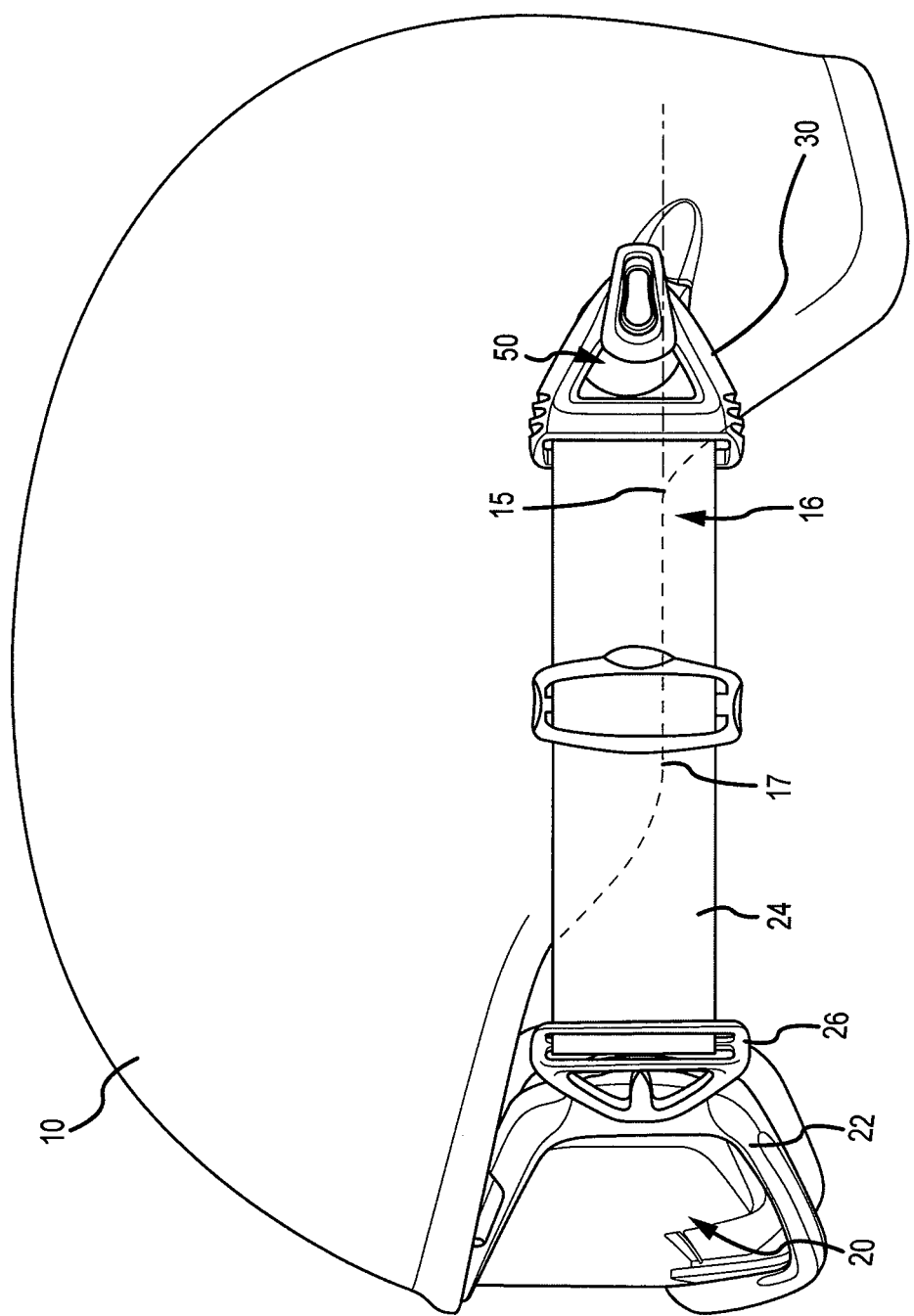
FIG. 5 is a profile drawing of a helmet and goggle having a goggle attachment system according to an embodiment of the invention.

FIG. 5 illustrates a goggle attachment system according to an embodiment of the invention. In some embodiments of the invention, the anchor 50 may be positioned on the helmet 10 along a path that naturally extends from the pivot point of the strap connector 26 attached to the lens assembly 22 when the goggle 20 is positioned on the wearer's face such that torque on the lens assembly 22 may be reduced or eliminated to improve fit and comfort of the goggle wearer. For example, as illustrated for the embodiment of FIG. 5, the anchor 50 may be positioned proximate an apex 15 of an ear cutout 16 of helmet 10. The anchor 50 may be positioned rearward and proximate the apex 15 in FIG. 5. In some embodiments, the anchor 50 is positioned so that when the post 34 is engaged in the anchor 50 the strap connector 30 pivots around a point that is approximately in line with an edge 17 of the ear cutout 16, or slightly above a ray extending along the edge 17. The position of the anchor 50 may also result in the goggle strap 24 being substantially horizontal when the goggle 20 is positioned on the wearer's face.

From the foregoing it will be appreciated that, although specific embodiments of the invention have been described herein for purposes of illustration, various modifications may be made without deviating from the spirit and scope of the invention. For example, although specific embodiments described herein have the post attached to the strap connector and the anchor located on the helmet, in other embodiments the post may be located on the helmet and the anchor that receives and engages the post is attached to the strap connector. Moreover, specific embodiments described herein include the anchor located on the exterior of the helmet. However, in alternative embodiments, the anchor may be positioned on an interior of the helmet to receive and engage the strap connector to attached the goggle to the helmet. Accordingly, the invention is not limited except as by the appended claims.

What is claimed is:

1. Protective wear, comprising:
   a goggle having first and second strap attachments coupled to a strap, the first strap attachment pivotally connected to a goggle assembly and the second strap attachment having a post fixedly attached to the second strap attachment; and
   a helmet having an anchor positioned in an opening in the helmet and oriented to position an anchor channel of the anchor to be in line with a recess formed on an exterior of the helmet, the anchor configured to receive the post and pivotally secure the post therein to attach the goggle to the helmet, the anchor further configured to release the post responsive to the second strap attachment pulled in a direction substantially parallel with the anchor channel of the anchor.

2. The protective wear of claim 1 wherein the strap is resilient.

3. The protective wear of claim 1 wherein the anchor comprises
   an anchor fitting having an opening in which the post is received;
   a clip adjacent the opening and configured to receive and clip the post in the anchor.

4. The protective wear of claim 3 wherein the anchor further comprises a magnet and the post includes a magnet.

5. The protective wear of claim 3 wherein the post includes a button portion and a channel portion, the clip engaging the channel to secure the post in the anchor.

6. The protective wear of claim 1 wherein the opening includes a recess in which the anchor is positioned.

7. The protective wear of claim 1 wherein the anchor includes a beveled surface at the transition from the helmet surface to the anchor.

8. The protective wear of claim 1 wherein the anchor is configured to receive the post in an anchor opening from a substantially perpendicular direction to engage and pivotally secure the post in the anchor.

9. The protective wear of claim 1 wherein the recess is formed at an angle downward relative to a horizontal plane.

10. The protective wear of claim 1 wherein the anchor is positioned rear of an apex of an ear cutout of the helmet.

11. The protective wear of claim 1 wherein the anchor is positioned approximately in line or above with an edge of an ear cutout.

12. The protective wear of claim 1 wherein the anchor is positioned on the helmet to provide a substantially horizontally oriented goggle strap when the goggle is positioned on a wearer's face.

13. The protective wear of claim 1 wherein the post is attached to a strap pull of the second strap attachment.

14. The protective wear of claim 1 wherein the second strap attachment further comprises a pull portion configured to be gripped and pulled when pulling the post from the anchor.

15. A goggle, comprising:
    a lens assembly;
    a first strap connector having a strap loop and configured to be pivotally attached to the lens assembly;
    a goggle strap attached to the strap loop of the first strap connector;
    a second strap connector having a strap loop to which the goggle strap is attached and the second strap connector further having a post fixedly attached to the second strap connector, the post configured to be received by and engaged with an anchor assembly of a helmet to provide a releasable and pivotal attachment to the helmet.

16. The goggle of claim 15 wherein the second strap connector comprises a strap pull having the strap loop and the post is connected to the strap pull.

17. The goggle of claim 16 wherein the strap pull includes a pull portion.

18. The goggle of claim 15 wherein the post is attached to the pull portion.

19. The goggle of claim 15 wherein the post includes a button portion and a channel portion.

20. The goggle of claim 19 wherein the button portion of the post includes a beveled surface.

21. The goggle of claim 15 wherein the second strap connector comprises a magnet disposed in the post.

22. The goggle of claim 15 wherein the lens assembly includes a goggle lens and a lens structure to which the goggle lens is attached and to which the first strap connector is pivotally attached.

23. The goggle of claim 15 wherein the second strap connector is configured to have a triangular shape, the strap loop along a side of the triangle and the post positioned proximate a corner opposite of the side of the triangle along the strap loop.

* * * * *